United States Patent
Kumagai et al.

(10) Patent No.: US 7,235,528 B2
(45) Date of Patent: Jun. 26, 2007

(54) IMMUNOPOTENTIATOR FOR MAMMARY GLAND OF DAIRY COWS CONTAINING LACTOFERRIN AS AN ACTIVE INGREDIENT

(75) Inventors: Katsuo Kumagai, Sendai (JP); Ken-ichi Komine, Sendai (JP); Kenzo Kai, Sendai (JP)

(73) Assignee: Kyoritsu Seiyaku Corporation, Tokyo (JP)

( * ) Notice: Subject to any disclaimer, the term of this patent is extended or adjusted under 35 U.S.C. 154(b) by 364 days.

(21) Appl. No.: 10/481,616

(22) PCT Filed: Jun. 24, 2002

(86) PCT No.: PCT/JP02/06266

§ 371 (c)(1), (2), (4) Date: Jun. 18, 2004

(87) PCT Pub. No.: WO03/002090

PCT Pub. Date: Jan. 9, 2003

(65) Prior Publication Data

US 2004/0235711 A1 Nov. 25, 2004

(30) Foreign Application Priority Data

Jun. 27, 2001 (JP) ............................. 2001-194652

(51) Int. Cl.
*A61K 38/40* (2006.01)
*C07K 14/79* (2006.01)

(52) U.S. Cl. ....................................... 514/12; 530/350

(58) Field of Classification Search ................... None
See application file for complete search history.

(56) References Cited

U.S. PATENT DOCUMENTS 5,658,581 A * 8/1997 De Lacharriere et al. ... 424/401
6,319,895 B1 * 11/2001 Tomita et al. .................. 514/8
6,562,820 B2 * 5/2003 Watts et al. ............. 514/235.5

FOREIGN PATENT DOCUMENTS

| EP | 0 474 506 A | 3/1992 |
|---|---|---|
| JP | 5-178759 A | 7/1993 |
| JP | 2000-041529 | 2/2000 |
| WO | WO 93/18061 A | 9/1993 |
| WO | WO 02/02121 A | 1/2002 |

OTHER PUBLICATIONS

W.C. Breau et al., "Growth inhibition of environmental mastitis pathogens during physiologic transitions of the bovine mammary gland", Veterinary Research, vol. 47, No. 2, Feb. 1986, pp. 218-222, XP001099011.

Ken-Ichi Asai et al., "Variation in $CD4^+$ T and $CD8^+$ T lymphocyte subpopulations in bovine mammary gland secretions during lactating and non-lactating periods", Veterinary Immunology and Immunopathology, 1998, pp. 51-61, vol. 65, Elsevier Science B.V.

T. Yamaguchi et al., "Differential Distribution of T Lymphocyte Subpopulations in the Bovine Mammary Gland During Lactation", 1999, pp. 1459-1464, vol. 82, Journal of Dairy Science.

* cited by examiner

*Primary Examiner*—Robert A. Wax
(74) *Attorney, Agent, or Firm*—The Nath Law Group; Gary M. Nath; Susanne M. Hopkins

(57) ABSTRACT

The invention provides an immunostimulant for a lactating bovine mammary gland, said immunostimulant containing lactoferrin or pharmaceutically acceptable salt thereof as an active ingredient.

3 Claims, 3 Drawing Sheets

IMMUNOPOTENTIATOR FOR MAMMARY GLAND OF DAIRY COWS CONTAINING LACTOFERRIN AS AN ACTIVE INGREDIENT

TECHNICAL FIELD

The present invention relates to an immunopotentiator for a lactating bovine mammary gland and to a method for immunopotentiation. In particular, the present invention relates to an immunopotentiator and a method for immunopotentiation that aims at the smooth transition of lactating bovine mammary glands from a lactation period to a dry period.

BACKGROUND ART

Dairy cattle become pregnant by fertilization during a lactation period. Five months after fertilization, the cattle begin to actively secrete hormones, such as estrogen, from their placentas and milk secretion decreases. As a result, part of the mammary gland tissue and cells start to regress.

As mammary glands in mother cattle regress, milk productivity is decreased while the fetal cows grow. Dairy farmers stop milking at an appropriate time in the precalving period in order to induce the mammary gland to enter the dry period. This will facilitate smooth parturition by dairy cattle and resumption of postcalving lactation.

During the dry period, new mammary tissue is generated and differentiated for suckling and feeding to newborn calves. This generation and differentiation occurs due to regression of the old mammary epithelium in the mucosal mammary tissue by apoptosis and the replacement ingression of various blood cells. When the generation and differentiation begins, mammary cells and tissues comprise extremely diverse constituent cells, including granulocytes, monocytes, macrophages, dendritic cells, NK cells, T-cells, B-cells and mast cells. Phagocytic cells such as granulocytes and macrophages are distributed in the mammary tissue and milk. Lymphocytes, such as helper CD4+ T-cells derived from the bloodstream and antibody-producing B-cells, are also distributed (Vet. Immunol. & Immunopathol., Vol. 65, 51–61, 1998; J. Dairy Sci., Vol. 82, 1459–1464, 1999). Thus, mammary gland resistance to infection is increased in the dry period.

The current method of inducing dairy cows to enter the dry period is to stop milking the cows in order to increase pressure within the mammary glands. However, in reality, some mammary glands of lactating cows struggle in the smooth transition to the dry period even with of the performance of this method. In such case, the cows encounter the problem that exogenous bacteria may easily infect the mammary glands resulting in an increased incidence of mastitis.

If the transition is delayed and troubled, the mammary gland of mother cows may be retarded. Further, when the mother cow raises calf, the calf may also encounter problems such as defective development, or be affected by infectious diarrhea caused by various bacteria or viruses.

These problems are serious to dairy farmers, and the earliest possible resolution of these problems is desired. However, no useful means to solve them has been found.

DISCLOSURE OF THE INVENTION

It is desirable, if there were an immunostimulant to enable the rapid transition of the mammary gland of lactating cows into the dry period. Furthermore, it is desirable, if there were an immunostimulant to enable the smooth development of the mammary gland and the formation of colostrum.

After extensive studies, the present inventors have found that the administration of a small amount of lactoferrin to mother cows can activate the immune system of the mother cows and enable the smooth transition of the mammary gland of mother cows from a lactation period to a dry period.

Thus, an embodiment of the present invention provides an immunopotentiator for the mammary glands of dairy cows that contains lactoferrin or pharmaceutically acceptable salt thereof as an active ingredient.

Another embodiment of the present invention further provides a method for the immunopotentiation of the mammary glands of dairy cows, said method comprising the administration of a pharmaceutical composition containing lactoferrin or pharmaceutically acceptable salt thereof as an active ingredient to lactating cows.

The present disclosure relates to subject matter contained in Japanese Patent Application No.2001-194652, filed on Jun. 27, 2001, the disclosure of which is expressly incorporated herein by reference in its entirety.

BEST MODE FOR CARRYING OUT THE INVENTION

Figure 1:
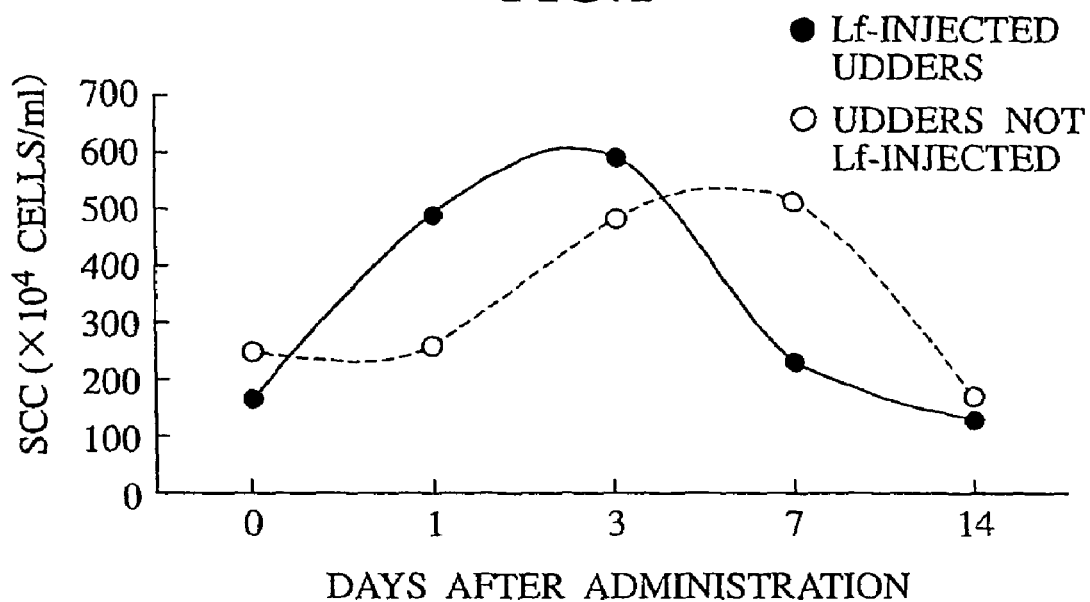
FIG. 1 is a graph showing changes in SCC in udders injected with Lf and those not injected with Lf.

The present invention is directed to an immunopotentiator for mammary gland of dairy cows.

The immunopotentiator comprises lactoferrin or pharmaceutically acceptable salt thereof as an active ingredient.

Lactoferrin (hereinafter referred to as "Lf") used in the present invention is a huge glycoprotein with a molecular weight of approximately 80,000, which is contained in the milk, saliva, tears, mucus from the bronchi, bile and intestinal fluids.

Pharmaceutically acceptable salts of Lf include any salts that are safe to mother cows and bovine fetuses, such as ammonium salt, alkali metal salt, hydrochloride, acetate and carbonate.

In the immunopotentiator, these Lf and Lf salts may be used alone or in combination with two or more thereof.

The Lf and Lf salts used in the present invention may be obtained from the milk of human, mammals, such as cows, goats or sheep, or may be obtained from transgenic animals or genetically engineered microorganisms.

Dosage forms of the present invention include, for example, ointment and liquid formulations. Bases used in the ointment include lipophilic and hydrophilic bases. The lipophilic base includes, for example, white petrolatum, yellow petrolatum, liquid paraffin, olive oil, peanut oil, soybean oil and lanolin. The hydrophilic base includes polyethylene glycol, sodium polyacrylate, stearyl alcohol, stearate, alminum stearate, glycerin, sodium alginate and carboxylmethylcellulose. Vehicles used for the liquid formulations include, in addition to those described above, for example, propylene glycol, polyethylene glycol and glycerin.

The pharmaceutical composition of the present invention may contain any additives. Additives include, for example, buffers, isotonization agents, stabilizers and preservatives.

This invention is also directed to a method for immunopotentiation of mammary glands of dairy cows by administrating the said agent to the dairy cows.

In consideration of the effect and economic efficiency achieved by administration, the dosage of the present invention is preferably 100–250 mg/udder, and more preferably 100–200 mg/udder of Lf equivalent. The Lf concentration in the milk is preferably 1000–2500 µg/ml, and more preferably 1000–2000 µg/ml, which is determined immediately after milking.

With regard to the number of doses, the above amount of a pharmaceutical composition maybe administered just once during a period beginning of the day of induction to the dry period with three weeks after the induction, or as often as every several days during and throughout the same period.

The dose forms of the present invention include, for example, infusion, preferably direct infusion, more preferably, injection into udders.

The invention will be more readily understood with reference to the following examples. However these examples are intended to illustrate the invention and are not to be construed as limiting the scope of the invention.

| (Formulation 1) | |
| --- | --- |
| Bovine lactoferrin | 100 mg |
| Sodium chloride | 80 mg |
| Potassium chloride | 2 mg |
| Potassium dihydrogenphosphate | 2 mg |
| Sodium dihydrogenphosphate | 2 mg |

The above compounds were mixed and the volume was adjusted to 10 ml with distilled water to obtain the liquid preparation of the present invention.

| (Formulation 2) | |
| --- | --- |
| Bovine lactoferrin | 100 mg |
| Cacao butter | 4 g |
| Ascorbic acid | 25 mg |
| Sodium chloride | 80 mg |

The above compounds were mixed and the volume was adjusted to 10 ml with distilled water to obtain the ointment of the present invention.

(Experiment 1)

The liquid preparation obtained in Formulation 1 was administered to 29 udders of lactating cows in good health on the day of induction to the dry period (0 day). The dosage of the liquid preparation was adjusted to 100–250 mg/udder of Lf equivalent. On the other hand, eleven udders of healthy lactating cows were treated without the liquid formulation.

Subsequently, somatic cell counts (referred to as SCC hereinafter) were determined in the milk of these cows. For comparison, SCC in the milk was also determined for the lactating cows without administration of Lf.

The SCC was determined on days 0,1, 3, 7 and 14 for the milk obtained from the group of udders injected with the liquid formulation (hereinafter referred to as Lf-injected udders) and that without injection of Lf (hereinafter referred to as udders without Lf-injection). The mean values were calculated for each sample. Determination of SCC was carried out by washing the test milk with 20 mM sodium ethylene bistetraacetic acid in phosphate buffered saline (EDTA-PBS) and staining with propidium iodide, followed by flow cytometry (FACSCalibur; Nippon Becton Dickinson Co., Ltd.).

The major part of somatic cells is leukocytes, which also appear in the milk in response to inflammation. At the time of transition to the dry period of the mammary glands of cows, the SCC in the milk is known to increase at first, and then return to its original value.

The results are shown in Table 1 and FIG. 1.

TABLE 1

Changes in SCC ($\times 10^4$ cells/ml)

| | Days after administration | | | | |
| --- | --- | --- | --- | --- | --- |
| | Day 0 | Day 1 | Day 3 | Day 7 | Day 14 |
| Lf-injected udders | 170.17 | 502.73 | 608.96 | 246.50 | 146.68 |
| Udders not Lf-injected | 250.26 | 256.65 | 492.65 | 528.07 | 180.58 |

As shown in Table 1 and FIG. 1, in the Lf-injected udders, SCC begins to increase immediately after administration, reaches a maximum on day 3, and then returns to approximately its original value.

In contrast, in the udders not injected with Lf, SCC begins to gradually increase after day 1, reaches a maximum on 6 day and then begins to decrease. It continues to decrease even on day 14 and SCC was not stabilized.

The maximum value of the Lf-injected udders was higher than that of the udders not Lf-injectioned.

The result shows that Lf promotes the migration of blood cells into the mammary tissue.

Accordingly, administration of Lf enables the early acquisition of a marked antibacterial effect.

(Experiment 2)

CD11b-positive cells, which are representative of phagocytic cells, were quantitatively determined for the milk used in experiment 1, which was obtained from the groups of the Lf-injected udders and the udders not Lf-injected.

Specifically, the cells in the milk were collected by centrifugation and stained with bovine monoclonal anti-CD11b antibody and FITC-labeled mouse monoclonal anti-IgG2b antibody. The number of the CD11b antigen-positive cells was determined by flow cytometry on day 0, 1, 3, 7 and 14. The numbers of the CD11b antigen-positive cells are shown in Table 2 and FIG. 2.

At the time of transition to the dry period, the number of CD11b antigen-positive cells in the mammary glands of cows generally increases and then returns to its original value. Thus, in order to investigate the influence of Lf on phagocytosis, the numbers of the CD11b antigen-positive cells were determined.

TABLE 2

Changes in the numbers of the CD11b antigen-positive cells (×10⁴ cells/ml)

| | Days after administration | | | | |
|---|---|---|---|---|---|
| | Day 0 | Day 1 | Day 3 | Day 7 | Day 14 |
| Lf-injected udders | 42.50 | 119.88 | 225.05 | 59.00 | 33.18 |
| Udders not Lf-injected | 55.31 | 40.41 | 164.79 | 148.21 | 24.74 |

Figure 2:
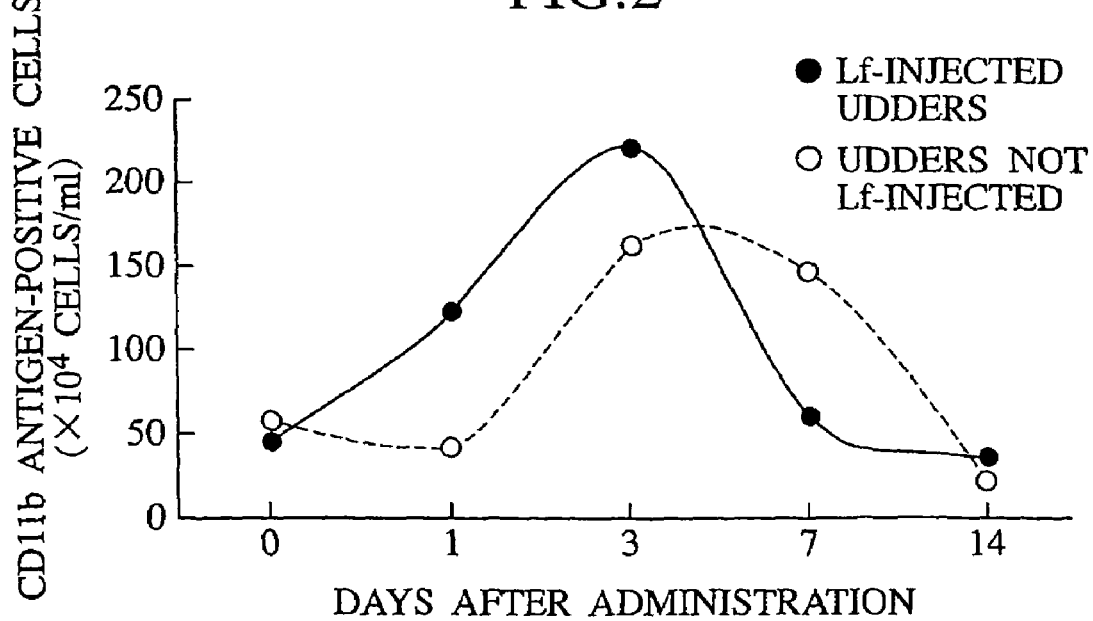
FIG. 2 is a graph showing changes in CD11b antigen-positive somatic cell counts in udders injected with Lf and those not injected with Lf.

As shown in Table 2 and FIG. 2, the number of the CD11b antigen-positive cells begins to increase immediately after administration, reaches a maximum on day 3, and then returns to its original value as early as day 7 in the Lf-injected udders.

In contrast, the number of the CD11b antigen-positive cells begins to increase after day 1, reaches a maximum on day 3 and then decreases in the udders not injected with Lf. The number continuously decreased, returning to its original value on day 14 and a stable number value could not obtained.

The maximum value of the Lf-injected udders was extremely high, compared to that reached by the udders not Lf-injected.

The result shows that blood cells increase rapidly and markedly in the Lf-injected udders compared to the udders not Lf-injected.

Accordingly, administration of Lf enables the early acquisition of a marked antibacterial effect.

(Experiment 3)

To investigate the effect of Lf on T lymphocytes, a member of immune response cells, $CD4^+T/CD8^+T$ cells were quantitatively determined for the milk used in experiment 1, which was obtained from the groups of the Lf-injected udders and the udders not Lf-injected.

Among the subtypes of T lymphocytes, $CD4^+T$ is known to be contained as a major component in the milk and mammary gland at the dry period and $CD8^+T$ as a major component in the lactation period. $CD4^+T$ cells are also known to act as helper T cells in the antibody production system, and $CD8^+T$ cells are also known to act as suppressive cells for antibody production.

Specifically, the experiment was carried out as follows: concentrations of $CD4^+T$ and $CD8^+T$ cells were determined for the milk used in experiment 1, which was obtained from the groups of the Lf-injected udders and the udders not Lf-injected. For determination, the $CD4^+T$ cells were stained with bovine monoclonal anti-CD4 antibody and FITC-labeled mouse monoclonal anti-IgG1 antibody, and the $CD8^+T$ cells were stained with bovine monoclonal anti-CD8 antibody and FITC-labeled mouse monoclonal anti-IgM antibody. The cells were subjected to flow cytometry for determination on days 0, 1, 3, 7 and 14. The mean values of the $CD4^+T/CD8^+T$ cells are shown in Table 3 and FIG. 3.

TABLE 3

Changes in the ratio of the concentration of the $CD4^+T/CD8^+T$ cells

| | Days after administration | | | | |
|---|---|---|---|---|---|
| | Day 0 | Day 1 | Day 3 | Day 7 | Day 14 |
| Lf-injected udders | 1.08 | 1.30 | 3.94 | 2.15 | 2.20 |
| Udders not Lf-injected | 1.01 | 1.38 | 1.63 | 1.93 | 2.05 |

Figure 3:
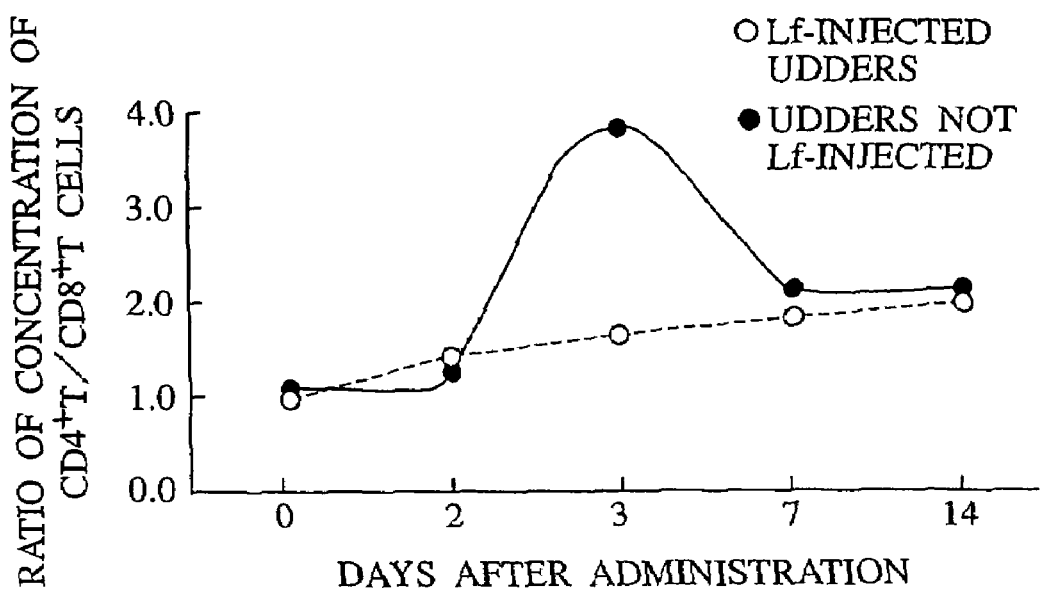
FIG. 3 is a graph showing changes in the ratio of concentration of the CD4$^+$T/CD8$^+$T cells in udders injected with Lf and those not injected with Lf.

As shown in Table 3 and FIG. 3, the $CD4^+T/CD8^+T$ value dramatically increases in the Lf-injected udders from day 2, which effect was retained until day 7. In contrast, the $CD4^+T/CD8^+T$ value slowly increases without any particular visible change in the udders not Lf-injected.

The result shows that the helper T/killer T cell ratio is greatly differs in the Lf-injected udders compared to the udder not Lf-injected.

Accordingly, administration of Lf enables the early transition of a mammary gland to the dry period.

(Experiment 4)

Subsequent to experiment 3, the ratio of concentration of $CD4^+T/CD8^+T$ was determined for each medium supplemented with Lf and with a combination of Lf and anti-Lf antibody in order to investigate the influence of the Lf on the $CD4^+T/CD8^+T$ cells.

Specifically, first of all the medium used herein was RPMI 1640 medium (Nissui Pharmaceutical Co., Ltd.) containing 5% fetal bovine serum. For the determination, lymphocytes were collected from the peripheral blood of healthy lactating cows by gradient centrifugation, and they were cultured for three days using (1) the medium, (2) the medium supplemented with 100 μg of Lf and (3) the medium supplemented with 100 μg of Lf and rabbit anti-bovine Lf affinity antibody with a titer that allows binding to 100 μg of Lf. The T lymphocyte subsets were analyzed using the flow cytometer before and three days after culturing. The results are shown in Table 4 and FIG. 4.

TABLE 4

Changes in the $CD4^+T/CD8^+T$ in the media

| | Days after administration | |
|---|---|---|
| | Day 0 | Day 3 |
| Medium | 2.03 | 1.84 |
| Lf (100 μg) | 2.03 | 3.46 |
| Lf (100 μg) + anti-Lf antibody | 2.03 | 1.47 |

Figure 4:
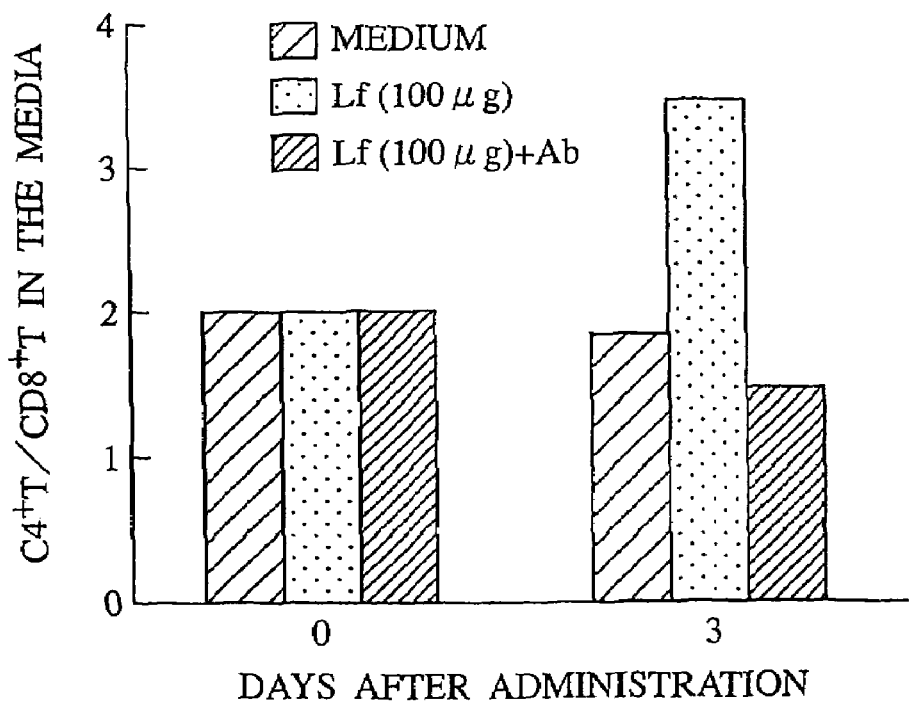
FIG. 4 is a graph showing changes in the ratio of concentration of the CD4$^+$T/CD8$^+$T cells in the media.

As shown in Table 4 and FIG. 4, the $CD4^+T/CD8^+T$ is increases significantly in the medium supplemented with Lf, compared to that of the medium without additives. In contrast, the $CD4+T/CD8^+T$ decreases in the medium supplemented with a combination of Lf and anti-Lf antibody, compared to that of the additive-free medium, indicating that the $CD4^+T/CD8^+T$ values are largely dependent on the Lf addition.

(Experiment 5)

The increase in immunity protein due to Lf was investigated. Immunoglobulin IgG, particularly IgG1, the most abundant species in the subclass, was used for the quantitative determination of the immunity protein.

Specifically, the experiment was carried out as follows: the liquid formation obtained in Formulation 1 was injected into 5 udders of healthy lactating cows on the day of induction into the dry period (day 0). The dose of the liquid formulation was adjusted to 100 mg/udder (concentration of 1000 μg/ml in the milk) calculated in terms of lactoferrin contained in the liquid formulation.

Three udders of healthy lactating cows were treated without the liquid preparation. The amount of IgG was determined for the milk obtained from the group of udders injected with the liquid preparation (hereinafter referred to as Lf-injected udders) and that not injected with Lf (hereinafter referred to as udders not Lf-injected) on days 0, 7, 14, 30, 14 days before calving and the day colostrum was obtained. The determination of the IgG1 concentration was carried out using single radial immunodiffusion (SRID), and the mean values of the IgG1 concentrations obtained were calculated. The results are shown in Table 5 and FIG. 5.

TABLE 5

Changes in the IgG1 concentrations

|  | Days after administration | | | | |
|---|---|---|---|---|---|
|  | Day 0 | Day 7 | Day 14 | 30 days before calving | 14 days before calving | formation of colostrum |
| Lf-injected udders | 3.6 | 8.6 | 17.2 | 42.7 | 55.2 | 52.1 |
| Udders not Lf-injected | 3.6 | 6.4 | 14.2 | 37.0 | 35.1 | 41.6 |

Figure 5:
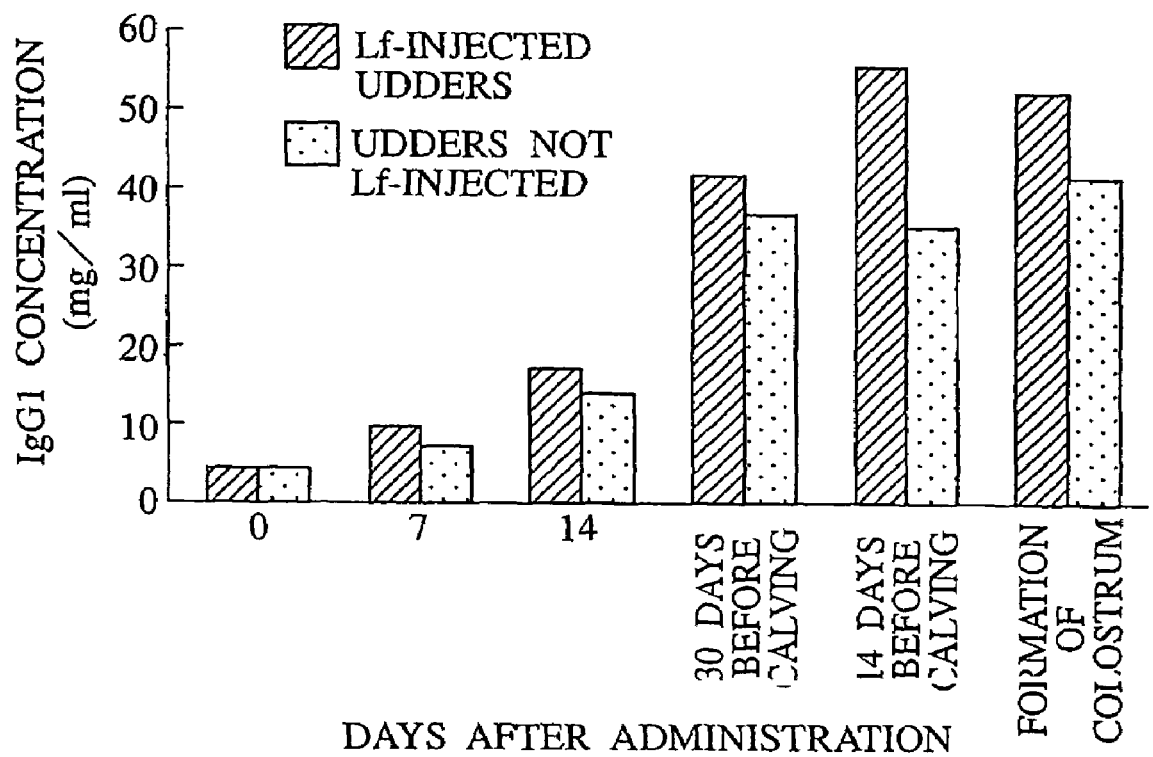
FIG. 5 is a graph showing changes in the IgG1 concentrations in udders injected with Lf and those not injected with Lf.

As shown in Table 5 and FIG. 5, increase of the IgG1 concentration is more prominent in the Lf-injected udders than in the udders not Lf-injected for the respective days tested.

Accordingly, administration of Lf has been shown to activate the immune system of the mammary gland in the dry period.

(Experiment 6)

To investigate the Lf-dependency of IgG1, concentrations of IgG1 were determined, as described in Experiment 5, using 10, 100, 200 and 500 mg of the Lf dose per udder. The results are shown in Table 6 and FIG. 6.

TABLE 6

The IgG1 concentrations for administration of Lf with each concentration

|  | Day 0 | Day 3 | Day 7 |
|---|---|---|---|
| Lf 10 mg | 4.10 | 4.20 | 4.50 |
| Lf 100 mg | 3.78 | 4.40 | 6.78 |
| Lf 200 mg | 4.70 | 7.73 | 13.60 |
| Lf 500 mg | 4.60 | 9.00 | 15.60 |

Figure 6:
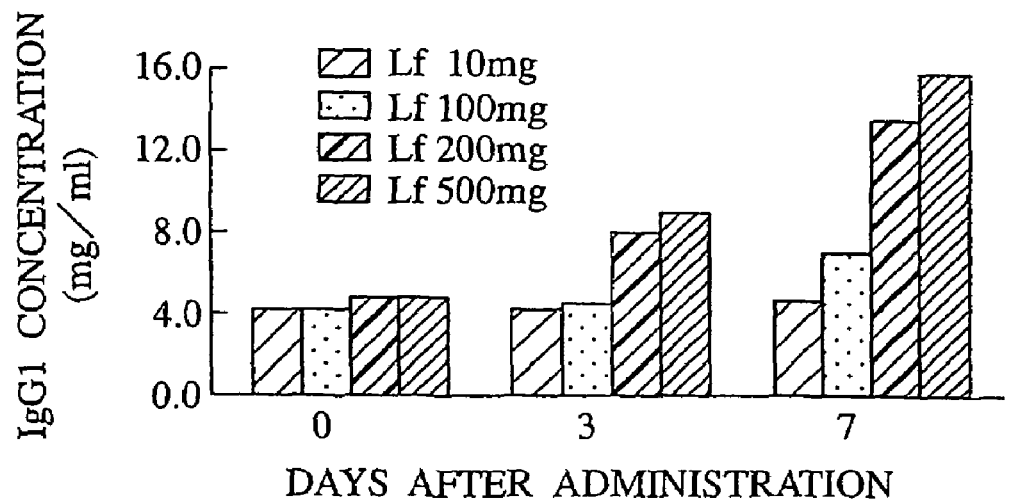
FIG. 6 is a graph showing changes in the IgG1 concentrations for different concentrations of Lf administered.

As shown in Table 6 and FIG. 6, increase of the IgG1 concentration is small when Lf is administered at a dosage of 10 mg. In contrast, the IgG1 concentration is significantly increased at a dosage of 100 mg or more. Accordingly, the result shows that administration of Lf at a dosage of 100 mg or more per udder will strongly stimulate IgG1 secretion.

(Experiment 7)

To test Lf for its antibacterial effect and therapeutic effect on mastitis, the liquid preparation according to Formulation 1 was administered to the 12 udders of cows in the dry period that were affected with mastitis. Among them, 8 were critically infected to mastitis. 4 were mildly infected with mastitis. The dose of the liquid preparation was adjusted to 100 mg/udder of Lf equivalent.

The states of mastitis and the numbers of bacteria were investigated

For comparison, dry-cow ointment, a remedy for mastitis in the dry period, was injected into the mammary glands of 29 udders affected with mastitis. Sephamedine DC, a product of Nippon Zenyakukogyo Co., Ltd., was used as the ointment.

Symptoms of mastitits were tested for the above-mentioned udders administered with Lf and those administered with the ointment until one week after calving. The cell numbers of staphylococcus, a major causative agent of mastitis, were also determined.

Determination of the staphylococcal cells was carried out as follows: milk was collected from the mammary glands at any time points between immediately before administration of Lf and six days after the administration, and the post-calving colostrum was diluted 1:10, 1:100 and 1:1000 with sterilized physiological saline, which was then plated on the agarmedium (No. 110 medium). The plates were cultured at 37° C. for 48 hours and the staphyloccal cells were counted based on the colonies formed on the agarmedium.

The symptoms of mastitis were examined by physical or by visual observation at the time when the liquid preparation containing Lf or the ointment was administered and a week after the calving.

The results for the udders administered the liquid preparation containing Lf are shown in Table 7, and those for the udders administered the ointment in Table 8.

In the table, the evaluations of the conditions of mastitis are represented by − for unaffected with mastitis, + for minor symptoms of mastitis, ++ for medium level of mastitis, and +++ for acute mastitis. The cell numbers of staphylococcus are indicated by colony forming units (CFU) per milliliter, and they are represented by − for $<2.0\times10^2$ CFU/ml, ± for $2.0\times10^2$ to $4.0\times10^2$ CFU/ml, + for $4.0\times102$ to $1.0\times10^3$ CFU/ml, ++ for $1.0\times10^2$ to $5.0\times10^3$ CFU/ml, and +++ for $>5.0\times10^3$ CFU/ml.

TABLE 7

Therapeutic effects of Lf administration and the cell numbers of *staphylococcus* (CFU/ml)

|  | Condition of mastitis at the time of administration | Cell number of *staphylococcus* at the time of administration | Condition of mastitis present at one week after calving | Cell number of *staphylococcus* in the colostrum |
|---|---|---|---|---|
| Case 1 | + | − | +++ | − |
| Case 2 | ++ | + | − | + |
| Case 3 | ++ | + | − | + |
| Case 4 | ++ | ++ | − | NT |
| Case 5 | ++ | +++ | − | NT |
| Case 6 | + | + | − | − |
| Case 7 | + | ++ | − | − |
| Case 8 | + | + | − | − |
| Case 9 | + | + | − | − |
| Case 10 | + | + | − | − |
| Case 11 | ++ | ++ | − | NT |
| Case 12 | ++ | + | − | NT |
|  |  |  | Incidence 8.3% | Positive rate 25% |

TABLE 8

Therapeutic effects of administration of the ointment
and the cell numbers of *staphylococcus* (CFU/ml)

| | Condition of mastitis at the time of administration | Cell number of *staphylococcus* at the time of administration | Condition of mastitis present at one week after calving | Cell number of *staphylococcus* in the colostrum |
|---|---|---|---|---|
| Case 1 | ++ | NT | + | + |
| Case 2 | ++ | NT | + | + |
| Case 3 | ++ | NT | + | ++ |
| Case 4 | ++ | NT | ++ | +++ |
| Case 5 | ++ | NT | + | ++ |
| Case 6 | ++ | NT | ++ | uncountable |
| Case 7 | ++ | NT | ++ | ++ |
| Case 8 | ++ | NT | ++ | +++ |
| Case 9 | ++ | NT | + | + |
| Case 10 | ++ | NT | + | + |
| Case 11 | ++ | + | ++ | ++ |
| Case 12 | +++ | NT | ++ | +++ |
| Case 13 | +++ | NT | ++ | ++ |
| Case 14 | +++ | NT | + | ++ |
| Case 15 | ++ | NT | − | + |
| Case 16 | ++ | NT | − | − |
| Case 17 | ++ | NT | − | − |
| Case 18 | ++ | NT | − | − |
| Case 19 | ++ | NT | − | − |
| Case 20 | ++ | NT | − | − |
| Case 21 | ++ | NT | − | − |
| Case 22 | ++ | NT | − | − |
| Case 23 | ++ | NT | − | − |
| Case 24 | ++ | NT | − | − |
| Case 25 | ++ | NT | − | − |
| Case 26 | ++ | NT | − | − |
| Case 27 | ++ | NT | − | + |
| Case 28 | ++ | NT | − | − |
| Case 29 | ++ | +++ | − | − |
| | | | Incidence 50% | Positive rate 55.2% |

As shown in Tables 7 and 8, the positive rate of staphylococcus (including +, ++ and +++) in the colostrum of the udders administered the liquid preparation containing Lf was 25%. It was 55.2% (16 out of 29 cases) in the colostrum of the udders administered the ointment.

Incidence of mastitis was 8.3% ((+, ++ and +++)/total cases) for the udders administered Lf, and was 50% (15/29 cases) for the udders administered the ointment.

Thus, it is appreciated that administration of Lf to lactating cows in the dry period may have therapeutic effects on mastitis.

(Experiment 8)

To investigate the preventive effects of Lf on mastitis, Lf was administered to lactating cows in the dry period without visible symptoms of mastitis, followed by the counting of the number of infected bacteria and the examination of the presence or absence of symptoms of mastitis.

Specifically, the liquid preparation according to. formulation 1 was injected into 17 udders of dry cows without visible symptoms of mastitis. The dose of the liquid formulation for infusion was 100 mg/udder of Lf equivalent.

For comparison, lactating cows in the dry period, without visible symptoms of mastitis were used for injection. Seventeen udders of these cows were injected with the ointment, as described in Experiment 7.

The above-mentioned udders administered with the liquid preparation containing Lf and those with the ointment were examined for symptoms of mastitis developed one week after calving. The cell numbers of *staphylococcus*, a major causative agent of mastitis, were also determined. The same method as described in Experiment 7 was used for the determination.

The results are shown in Tables 9 and 10. Each evaluation was according to Experiment 7.

TABLE 9

Preventive effects of LF-administration and the cell
numbers of *staphylococcus* (CFU/ml)

| | Number of Staphylococcal cells | Condition of mastitis by one week after calving | Number of Staphylococcal cells in the colostrum |
|---|---|---|---|
| Case 1 | − | − | + |
| Case 2 | − | − | − |
| Case 3 | − | − | − |
| Case 4 | − | − | − |
| Case 5 | − | − | + |
| Case 6 | − | − | − |
| Case 7 | − | − | − |
| Case 8 | − | − | − |
| Case 9 | − | − | − |
| Case 10 | − | − | − |
| Case 11 | − | − | − |
| Case 12 | − | − | NT |
| Case 13 | − | − | − |
| Case 14 | − | − | − |
| Case 15 | − | − | − |
| Case 16 | + | − | − |
| Case 17 | + | − | − |
| | | Incidence 0% | Positive rate 11.8% |

TABLE 10

Preventive effects of the ointment-administration and
the cell numbers of *staphylococcus* (CFU/ml)

| | Number of Staphylococcal cells | Condition of mastitis by one week after calving | Number of Staphylococcal cells in the colostrum |
|---|---|---|---|
| Case 1 | NT | ++ | +++ |
| Case 2 | NT | ++ | +++ |
| Case 3 | NT | ++ | +++ |
| Case 4 | NT | ++ | +++ |
| Case 5 | NT | + | +++ |
| Case 6 | NT | + | + |
| Case 7 | − | + | ++ |
| Case 8 | − | + | ++ |
| Case 9 | NT | − | − |
| Case 10 | NT | − | − |
| Case 11 | NT | − | − |
| Case 12 | − | − | − |
| Case 13 | NT | − | + |
| Case 14 | − | − | − |
| Case 15 | − | − | − |
| Case 16 | − | − | + |
| Case 17 | NT | − | − |
| | | Incidence 47.1% | Positive rate 58.8% |

As shown in Tables 9 and 10, the incidence of mastitis ((+, ++ and +++)/total cases) was 0% for the udders administered with the liquid preparation containing Lf, and 47.1% for the udders administered with the ointment.

Regarding the staphylococcal cells, the positive rate of staphylococcus ((+, ++ and +++)/total determined cases: 2/17 cases) was 11.8% for the colostrum from the udders administered with the liquid preparation containing Lf, and 55.8% (10/17 cases) for the colostrum from the udders administered with the ointment.

Thus, it is appreciated that administration of Lf to lactating cows in the dry period may have preventive effects against mastitis.

INDISTRIAL APPLICABILITY

The embodiment of the present invention enables to stimulate the activation of the immune system in the mammary glands of lactating cows.

The embodiment of the invention also enables the smooth and rapid transition of the mammary glands of lactating cows from the lactation period to a dry period.

Furthermore, the embodiment of the invention enables the formation of clean colostrum with less contamination by bacteria and enables the migration of antibodies into calves, thereby contributing to the prevention of the defective development of calves.

The embodiment of the invention further enables the smooth transition in the perinatal period, including calving, formation of colotstrum, initiaitin of the secretion of mature milk, etc.

The embodiment of the invention enables the prevention of direct infection of the mammary gland of mother cows with bacteria during the transition period between lactation and dry periods or during the dry period.

The embodiment of the invention further enables the prevention of mastitis during the transition period between lactation and dry periods or during the dry period.

The invention claimed is:

1. A method for a smooth transition of a mammary gland of a lactating bovine from a lactation period to a dry period, comprising the step of locally administering to a lactating bovine a therapeutically effective amount of a pharmaceutical composition comprising lactoferrin or a pharmaceutically acceptable salt thereof.

2. The method according to claim 1, wherein locally administering comprises intramammary administration.

3. The method according to claim 2, wherein the pharmaceutical composition is administered in an amount of from 100 mg/udder to 250 mg/udder of lactoferrin equivalent.

* * * * *

UNITED STATES PATENT AND TRADEMARK OFFICE
CERTIFICATE OF CORRECTION

PATENT NO.       : 7,235,528 B2
APPLICATION NO.  : 10/481616
DATED            : June 26, 2007
INVENTOR(S)      : Kumagai et al.

Page 1 of 1

It is certified that error appears in the above-identified patent and that said Letters Patent is hereby corrected as shown below:

Title Page, Item (73) Assignee:
Please add the second Assignee under the first Assignee
-- T-CELL RESEARCH INSTITUTE, Miyagi, (JP) --

Signed and Sealed this

Twenty-fifth Day of August, 2009

David J. Kappos
*Director of the United States Patent and Trademark Office*